US00PP12496P2

(12) United States Plant Patent
Utecht

(10) Patent No.: US PP12,496 P2
(45) Date of Patent: Mar. 26, 2002

(54) GERANIUM PLANT NAMED 'FISSALMROSE'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/773,008

(22) Filed: Jan. 31, 2001

(51) Int. Cl.[7] ..... A01H 5/00
(52) U.S. Cl. ..... Plt./328
(58) Field of Search ..... Plt./327, 328

(56) References Cited

PUBLICATIONS

GTITM UPOVROM Citation for 'FISSALMROSE' as per QZ PBR 991466; Oct. 20, 1999.

Official Gazette of the Community Plant Variety Office Dec. 15, 1999; European Union application, denomination, and decision for 'FISSALMROSE'.

German Application for 'FISSALMROSE' Dec. 15, 1998.

German Proposed Denomination for 'FISSALMROSE' Sep. 15, 1999.

Canadian Application, proposed denomination, Plant Varieties Journal, No. 38; Jan., 2001 (Canada), p. 49.

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fissalmrose', as described and illustrated, and particularly characterized by the combined features of bright rose flower color, very large umbels, medium-green, zoned foliage, vigorous growth, and relatively wide plant habit.

1 Drawing Sheet

BACKGROUND OF THE INVENTION

The present invention comprises a new and distinct cultivar of geranium, botanically known as *Pelargonium zonale*, and hereinafter referred to by the cultivar name 'Fissalmrose'.

'Fissalmrose' is a product of a planned breeding program which had the objective of creating new geranium varieties with uniformly deep salmon or salmon-pink flower color, in combination with medium-green foliage.

'Fissalmrose' originated from a hybridization made by the inventor Angelika Utecht in a controlled breeding program in Galdar, Gran Canaria, Spain, in 1996.

The female parent was a hybrid seedling, No. 1216-3 (unpatented), having uniform salmon colored, single-type flowers, light to medium-green foliage with strong zonation, and vigorous growth. The male parent of 'Fissalmrose' was the variety 'Fiseye', U.S. Plant Pat. No. 11,302, which is characterized by light-violet flowers with large red eyes on petals, and large, medium green leaves without zonation.

'Fissalmrose' was selected as one flowering plant within the progeny of the stated cross by Angelika Utecht in 1997 in a controlled environment in Galdar, Gran Canaria, Spain. The first act of asexual reproduction of 'Fissalmrose' was accomplished when vegetative cuttings were taken from the initial selection in the fall of 1997 in a controlled environment in Galdar, Gran Canaria, Spain, by, or under the supervision of, Angelika Utecht.

Horticultural examination of plants grown from cuttings of the plant initiated in May 1998 in Hillscheid, Federal Republic of Germany, and continuing thereafter, has demonstrated that the combination of characteristics as herein disclosed for 'Fissalmrose' are firmly fixed and are retained through successive generations of asexual reproduction.

'Fissalmrose' has not been observed under all possible environmental conditions. The phenotype may vary significantly with variations in environment such as temperature, light intensity, and day length.

BRIEF DESCRIPTION OF THE INVENTION

The following observations, measurements, and comparisons describe plants grown in Hillscheid, Germany, and in Langley, British Columbia, Canada, under greenhouse conditions which approximate those generally used in commercial practice.

The following traits have been repeatedly observed and are determined to be basic characteristics of 'Fissalmrose' in combination distinguish this geranium as a new and distinct cultivar:

1. Bright rose colored, weakly semi-double flowers;
2. Large, roundflowers and very wide inflorescences;
3. Medium green foliage with distinct zonation;
4. Vigorous growth, and relatively tall plant habit; and
5. Mid season spring flowering response.

Of the many commercial cultivars known to the present inventor, the most similar in comparison to 'Fissalmrose' is the variety 'Fisrorose', United States plant patent applied for, Ser. No. 09/632,244.

In comparison to 'Fisrorose', 'Fissalmrose' has a more intense flower color, longer peduncles, weaker anthocyanin coloration of pedicels and sepals, and not quite as strong zonation on leaves.

BRIEF DESCRIPTION OF THE DRAWING

The accompanying photographic drawing shows typical flower and foliage characteristics of 'Fissalmrose' with colors being as true as possible with an illustration of this type. The photograph shows a flowering potted plant.

The measurements were taken in Langley, British Columbia, Canada, on Jul. 20, 2000, 15 weeks after planting of rooted cuttings into 6 inch pots. The plants had not been pinched.

In the following description color references are made to The Royal Horticultural Society Colour Chart (R.H.S.). The color values were determined indoors from plants developed in a green-house in May 2000 in Hillscheid, Germany.

Classification:

*Botanical.*—A hybrid of the species *Pelargonium zonale* L'Hérit.

*Commercial.*—Zonal geranium, cv. 'Fissalmrose'.

Inflorescence:

*Umbel.*—Shape: Umbrella-shaped. Average diameter: 123 mm. Average depth: 65 mm. Peduncle length: 228 mm. Peduncle color: Light green, RHS 143 B to 143 C. Pedicel length: 34 mm. Pedicel color: Light green, RHS 143 C, slight infusion of anthocyanin, light brownish-red, RHS 179 B. Number of flowers per umbel: Approximately 30–40. Lastingness of individual bloom: Approximately 9 days at 18° C. Lastingness of umbel: Approximately 18 days.

*Corolla.*—Average diameter: 47 mm. Form: Weakly semi-double. Shape: Nearly round, open, slightly cup-shaped. Number of petals: 6–7. Petals size: Upper petals (2): 25–27 mm in length; 20 mm in diameter, Lower petals: 23–25 mm in length, 20–23 mm in diameter. Inner petals are smaller in size. Petal shape: Oblong to nearly obovate, with the upper end rounded and with attenuate base, margin entire. Color (general tonality from a distance of three meters): Uniform rose-pink. Color of upper petals: Color varying between RHS 52 A and closest to but more intense than RHS 52 B. Markings of upper petals: Absent. Color of lower petals: Coloration between RHS 50 B–52 B, no markings. Color of lower surface of petals: Salmon pink, RHS43 C. Color of sepals: Light green, RHS 143 A–B (varies between the two colors provided), very weak brownish hue at the base, RHS 179 B. Number of sepals: 5. Sepal size: 11–12 mm in length, 4 mm in diameter for the upper sepal, 2–3 mm in diameter for the other petals. Sepal shape: Linear to lanceolate, acute tip, base truncate, margin entire. Number of petaloids: 1–3. Petaloid color: Upper surface color varying between 52A and 52B, lower surface RHS 50B.

*Bud: (just prior to petals unfolding).*—Shape: Elliptical. Color (lower part — sepals): Light green, RHS 143 B, no anthocyanin. Color (upper part — petals): Salmon, slightly marbled, Varying between RHS 43 B and RHS 43 D. Length: 17 mm. Width: 9 mm.

*Reproductive organs.*—Androecium: 5 fertile anthers, white filaments, orange pollen. Gynoecium: 5–6-lobed, pink stigma, RHS 52 C, light pink style. Fertility/seed set: A few seeds are developed, mainly from late summer to fall. Pollen produced: Moderate quantity, color RHS 30 A. Number of pistils: One.

*Spring flowering response period.*—In Hillscheid, Germany, in 2000, plants had on average 0.8 flowers opened 8 weeks after planting of rooted cuttings.

*Outdoor flower production.*—Only moderately floriferous, due to the large size of the inflorescences, the flower count in 2000 in Hillscheid, Germany, indicated about 2–3 inflorescence per plant in mid May.

*Durability.*—Relatively good rain resistance, some fading of flower color (RHS 55A) may occur.

*Lastingness of individual bloom.*—Approximately 9 days at 18° C.

*Fragrance.*—None.

Plant:

*Foliage.*—Form: Kidney-shaped, with nearly closed base, slightly wavy margin, very weak expression of lobes. Margin: Bicrenated. Size of leaf: 60 mm long, 105 mm wide. Color of upper surface: Light green, approximately RHS 137 B–C (varies between two color designations), dull and slightly velvety. Color of lower surface: RHS 137 D. Zonation: Wide, but not very strong, brown, approximately RHS 166 A. Petiole size: 60–70 mm in length, 3–4 mm in diameter. Petiole color: Light green, RHS 143 C.

*General appearance and form.*—Stem color: Green, RHS 143 A. Internode length: 25–30 mm. Branching pattern: 5.0 branches. Plant size: 25.5 cm from soil to surface of foliage canopy/40 cm in diameter.

Disease/pest resistance/susceptibility: None observed to date.

I claim:

1. A new and distinct cultivar of geranium plant named 'Fissalmrose', as described and illustrated.

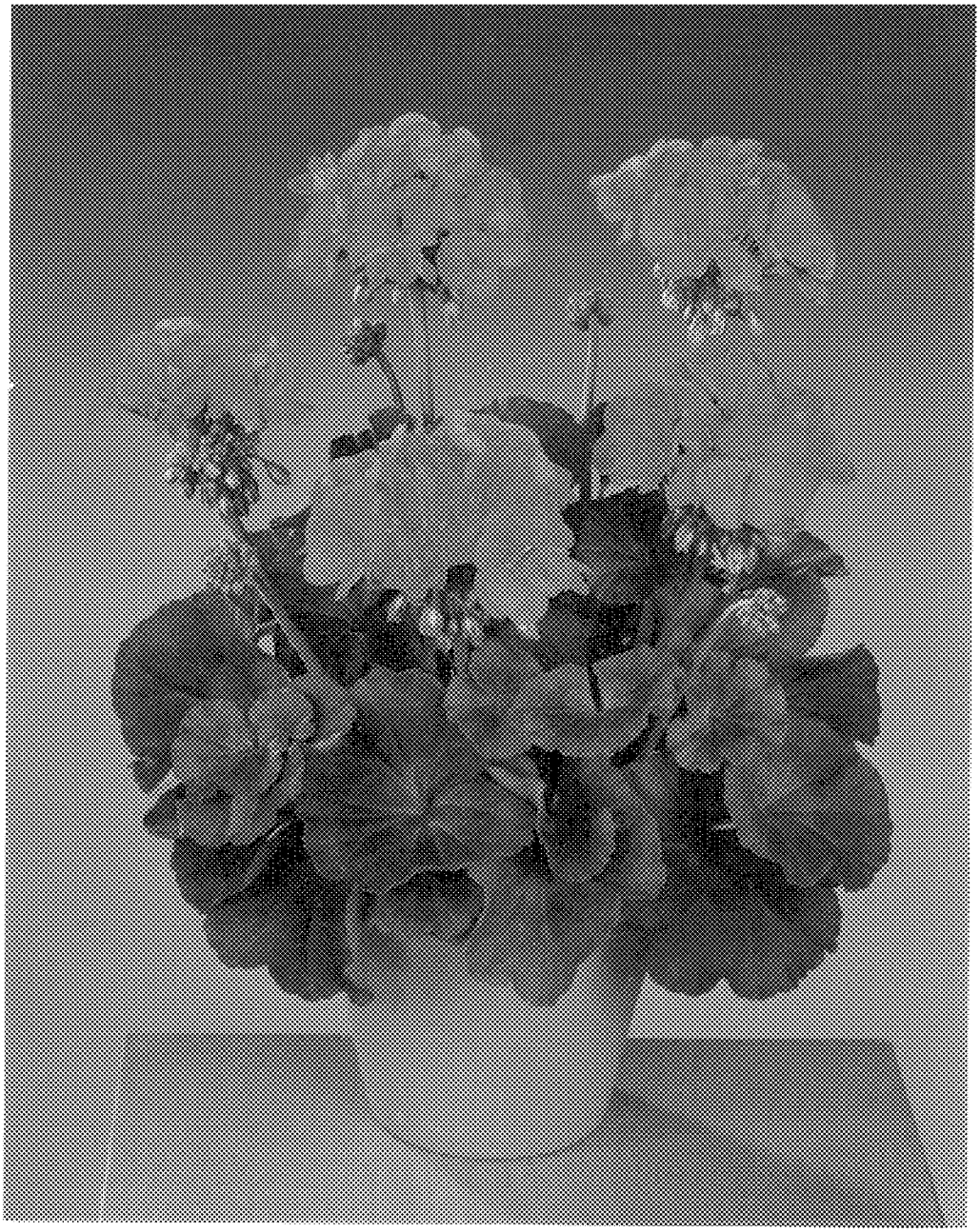

* * * * *